United States Patent [19]
Daher et al.

[11] Patent Number: 5,874,108
[45] Date of Patent: Feb. 23, 1999

[54] SALT COATED TABLET

[75] Inventors: Lawrence J. Daher, Elkhart; Robbie L. Hayward, Mishawaka; Lonnie C. Sackman, Elkhart, all of Ind.

[73] Assignee: Bayer Corporation, Morristown, N.J.

[21] Appl. No.: 907,707

[22] Filed: Aug. 8, 1997

[51] Int. Cl.[6] .............................. A61K 9/20; A61K 9/28
[52] U.S. Cl. ........................ 424/464; 424/465; 424/474
[58] Field of Search .................................. 424/1.61, 474, 424/464, 465, 484

[56] References Cited

U.S. PATENT DOCUMENTS 5,641,513   6/1997   Lech et al. ............................... 424/474

*Primary Examiner*—Thurman K. Page
*Assistant Examiner*—Sharon Howard
*Attorney, Agent, or Firm*—Mary G. Boguslaski

[57] ABSTRACT

The invention provides a coated tablet, a coating composition and a method of film coating. The coating is particularly useful for pharmaceutical tablets. The coating composition is composed of an aqueous solution of film forming inorganic salts which may be used with conventional coating techniques. Such film forming salts include sodium polyphosphate and sodium sulfate. This coating may be used on uncoated tablet cores, as a final coating or used as a subcoating for other coatings, such as enteric coatings. Use of this coating composition provides savings in cost of materials and in manufacturing efficiency over previous polymeric cellulose coatings.

12 Claims, No Drawings

SALT COATED TABLET

FIELD OF THE INVENTION

The invention is related to film coating tablets or caplets with an aqueous salt solution.

BACKGROUND OF THE INVENTION

In the pharmaceutical industry tablets and caplets have been coated in many ways to enhance their market appeal and to enhance their swallowability. Early work generally used sugar coatings. Later polymer coatings, often requiring the use of non-aqueous solutions, were popular, but because of environmental concerns were replaced at least in the United States by aqueous coating techniques. Thin coatings of cellulose polymers are commonly used to enhance swallowability and as undercoatings to facilitate the addition of other coatings, such as enteric coatings.

SUMMARY OF THE INVENTION

This invention provides a new coating composition, a method of use and a tablet coated with a sufficient amount of the composition to cover all surfaces of the tablet. The composition may be spray coated onto uncoated tablet cores in aqueous solution, or used as a final coating on top of a subcoated tablet. The composition is based on the use of a film forming salt. Alkali salts of edible inorganic acids are examples of such film forming salts. Sodium polyphosphate and sodium sulfate are preferred. The coating composition may also contain dyes, and formulation assistants such as lubricants, drying agents and suspending agents as desirable to provide the final film characteristics.

DETAILED DESCRIPTION OF THE PREFERRED EMBODIMENTS OF THE INVENTION

This invention provides an aqueous film coating composition useful for the coating of pharmaceutical tablets. Tablets are coated with an amount of coating material sufficient to cover the surface of the tablet. Generally such a coating will impart a weight gain of from about 0.3% to about 7.0% depending on the size of the tablet, the coating color, if any, and the degree of coating desired. The coating composition contains a film forming salt. Film forming salts are ones which, when deposited on a pharmaceutical tablet and dried, will form a film similar to those formed by cellulosic polymers such as hydroxypropylmethyl or hydroxypropyl cellulose.

Film forming salts include alkali salts of inorganic acids which are suitable for human consumption such as phosphates or sulfates. Preferred salts are sodium polyphosphate and sodium sulfate. Sodium polyphosphate is most preferred. Given the disclosure herein, those of ordinary skill in the art of tablet coating will be able to identify additional film forming salts, which are considered equivalent to those named.

Sodium polyphosphate forms clear films when deposited from aqueous solutions. If a clear tablet coating is desired, a simple solution of sodium polyphosphate in water can be applied to tablets, in any conventional way of coating tablets, to form clear film coated tablets. Such salt based coatings provide a very low cost alternative to hydroxypropylmethyl cellulose and hydroxypropyl cellulose based coatings. Savings may be as high as 90% of the cost of commercially purchased cellulose polymer based coating compositions. In addition, because of the high solids content of these salt coating compositions, application time may be reduced, providing additional savings in increased output and lower per unit processing costs.

Formulation assistants may be desirable for some coatings and suitable processing parameters may be identified by those of skill in the art of tablet coating. Such formulation assistants may include surfactants for substrate wetting and coating leveling properties, dyes and/or pigments, suspending agents, lubricants and drying aids. The table below provides guidance to useful formulation assistants but should not be construed to provide the only or even most preferred compounds:

| | |
|---|---|
| Surfactants | lecithin |
| | sodium stearoyl lactylate |
| Drying aids | Magnesium carbonate |
| | magnesium sulfate |
| | sodium sulfate |
| Lubricants | Distilled monoglyceride dispersion (Myvatex SSH) |
| | propylene glycol monostearate |
| | glyceryl monooleate |
| Suspending agents | magnesium aluminum silicate |
| | calcium silicate |

In addition, dyes and pigments such as commercially available FD&C dyes, natural dyes such as San Red F, flavorants, sweeteners, and odorants may be added for their customary purpose. The wide range of natural and artificial colors, surfactants, may be added as is well known to those of skill in the art and science of tablet coating.

In general the coating composition is predominantly made up of the film forming salt in water, preferably from about 5 to about 20% by weight of the film forming salt in water, most preferably from about 10 to about 15% by weight. Dyes and formulation assistants may be added. Preferred and most preferred (approximate) weight ranges in aqueous solution for some examples of possible formulation assistants are given below. Other formulation assistants may be used as will be apparent to those of ordinary skill in the art.

| | Preferred | Most preferred |
|---|---|---|
| suspending agent | 0 to 1.5% | 0.5% to 1.5% |
| lubricant | 0 to 1.5% | 0.5% to 1.5% |
| drying agent | 0 to 10% | 1.0 to 10% |
| surfactant | 0 to 1.2% | 0.2% to 1.2% |

The aqueous coating composition is prepared according to the physical properties of its constituents, i.e. soluble materials are dissolved, insoluble materials are dispersed. The type of mixing used is also based on the properties of the ingredients. Low shear liquid mixing is used for soluble materials and high shear liquid mixing is used for insoluble materials. In the examples provided herein, lecithin, titanium dioxide, magnesium aluminum silicate and Myvatex SSH require high shear dispersion, while all other ingredients can be dissolved using low shear mixing. Alternatively, high shear may be used for all ingredients. Heating is not required in the preparation of the coating composition.

The coating composition may be applied by any of the usual pharmaceutical coating processes and equipment. Tablets may be coated is fluid bed equipment, rotating coating pans, or by dipping. Fluid bed equipment, and the widely used rotating coating pans, are particularly useful when the composition is applied by atomized spray.

Heated air is used in fluid bed equipment and in the rotating coating pan method to dry the sprayed tablets, in a way that allows continuous spraying while the tablets are being simultaneously dried. Discontinuous, or intermittent spraying, may also be used, but generally requires longer coating cycles and is therefore not preferred.

Tablets may be coated directly, i.e. without a subcoat to prepare the surface. Subcoats may of course be used, if desired, but are not generally required. Topcoats may also be used, but are generally not required. If a topcoat is used, it must be formulated with the salty character of the coating in mind. Topcoats of cellulosic polymer dispersions may precipitate during drying if used with the salt coating of this invention.

The coating composition of this invention is not limited to any particular active ingredient or range of active ingredients. Various pharmaceutical tablets or caplets, based on the normal range of excipients, and so forth may all be coated as described.

EXAMPLES

Example 1
Clear coating

A coating composition containing sodium polyphosphate as the salt film former:

| ingredient | % w/w |
|---|---|
| lecithin | 0.1 |
| sodium polyphosphate | 10.0 |
| water | 89.9 |
| | 100.0 | provides a clear coating for tablets or caplets. The salt is dissolved in water using no heat and the lecithin added and mixed using high shear. The coating composition may be applied using conventional spray coating equipment. This composition was applied to caplets in a 6 inch Wurster column, using an air inlet temperature of about 70 degrees Centigrade and an exhaust temperature of about 50 degrees Centigrade.

Example 2
Opaque Coating I-Yellow

When an opaque colored coating is desired, suitable additives may be added to a sodium polyphosphate solution. A typical opaque, bright yellow coating composition, compounded for spray application in perforated pan coating equipment, is provided below:

| Ingredient | % w/w |
|---|---|
| FD&C Yellow No. 5 | 1.37 |
| sodium stearoyl lactylate | 0.50 |
| titanium dioxide | 3.00 |
| magnesium aluminum silicate | 1.00 |
| Myvatex SSH | 0.20 |
| magnesium sulfate, heptahydrate | 6.90 |
| sodium polyphosphate | 12.90 |
| water | 74.13 |
| | 100.00 |

Myvatex SSH is an aqueous dispersion of distilled monoglycerides, available from Eastman Chemical Company, located at Rochester, N.Y. 14603. It is used as a lubricant for smooth tablet to tablet flow during pan coating. Other lubricants with similar solubility characteristics may also be used. Other dyes, pigments, wetting and suspending agents may also be used. Veegum K is a preferred form of magnesium aluminum silicate which may be purchased from RT Vanderbilt Company, Inc. located at 30 Winfield Street, Norwalk, Conn. 06855.

This coating, and that provided in Example 3, was applied to caplets in a 24 inch Accela Cota coating pan. The pan was rotated at 7 RPM. The average application time was 40 minutes. The inlet air temperature was between about 100 and about 115 degrees Centigrade. The outlet air temperature was between about 40 and 65 degrees Centigrade. The Tablet bed temperature was between about 60 and 62 degrees Centigrade.

Example 3
Opaque Coating II-Light Purple

Another opaque coating formulation compounded for spray application in perforated pan coating equipment is provided below:

| Ingredient | % w/w |
|---|---|
| San Red F | 0.74 |
| sodium stearoyl lactylate | 0.53 |
| titanium dioxide | 3.19 |
| magnesium aluminum silicate | 1.06 |
| Myvatex SSH | 0.21 |
| magnesium sulfate, heptahydrate | 7.71 |
| sodium potyphosphate | 13.72 |
| water | 72.84 |
| | 100.00 |

San Red F is a water soluble natural dye obtained from beets and available from SAN-El Chemical Industries located at 1-11 Sana-cho 1-Chome, Toyohaka, Osada, 561 Japan. An Accela Cota coating pan was used as described above. The average application rate was about 50 grams/per minute. The total coating time was about 25 minutes. The inlet air temperature was between about 105 and about 115 degrees Centigrade. The outlet air temperature was between about 45 and 65 degrees Centigrade. The tablet bed temperature was about 60 to 65 degrees Centigrade.

Obviously many modifications and variations of the invention as set forth may be made without departing from the spirit or scope of the invention which is defined by the claims herein.

What is claimed is:

1. A method of preparing a salt coated tablet, comprising the steps of:
    a. preparing an aqueous solution of from about 5 to about 20% by weight of a film forming salt component; and
    b. spray coating a tablet with such aqueous solution.
2. The method of claim 1 in which the aqueous solution also contains a drying aid.
3. The method of claim 1 in which the aqueous solution also contains a lubricant.
4. The method of claim 1 in which the aqueous solution also contains a suspending agent.
5. The method of claim 1 in which the aqueous solution is prepared without heating.
6. An aqueous coating composition comprising
    a. from about 5 to about 20% by weight of a film forming salt;
    b. from about 0 to about 1.5% by weight of a suspending agent;
    c. from about 0 to about 10% by weight of a drying agent;
    d. from about 0 to about 1.5% by weight of a lubricant; and e. from about 0 to about 1.2% by weight of a surfactant.

7. A coated tablet comprising a) an uncoated tablet core containing active ingredients; and b) a salt coating sufficient to cover the surface of the tablet.

8. The coated tablet of claim 7 wherein the salt coating is applied as an aqueous solution of a film forming salt component.

9. The coated tablet of claim 8 in which the film forming salt component constitutes from about 5 to about 20% by weight of the coating solution.

10. The coated tablet of claim 9 in which the film forming salt component constitutes from about 10 to about 15% by weight of the coating solution.

11. The coated tablet of claim 8 in which the film forming salt component is an alkali salt of an edible inorganic acid.

12. A coated tablet comprising:

a) an uncoated tablet core containing active ingredients; and b) a salt coating sufficient to cover the surface of the tablet, the salt coating applied as an aqueous solution of a film forming salt component selected from the group consisting of sodium polyphosphate and sodium sulfate.

\* \* \* \* \*